United States Patent
Klatzmann et al.

(10) Patent No.: US 6,872,528 B2
(45) Date of Patent: Mar. 29, 2005

(54) HIGHLY PRODUCTIVE PACKAGING LINES

(75) Inventors: David Klatzmann, Paris (FR); Jean-Loup Salzmann, Paris (FR)

(73) Assignee: Universite Pierre et Marie Curie, Paris (FR)

( * ) Notice: Subject to any disclaimer, the term of this patent is extended or adjusted under 35 U.S.C. 154(b) by 272 days.

(21) Appl. No.: 09/978,931

(22) Filed: Oct. 15, 2001

(65) Prior Publication Data

US 2002/0123146 A1 Sep. 5, 2002

Related U.S. Application Data

(63) Continuation of application No. 09/231,834, filed on Jan. 16, 1999, now abandoned, which is a continuation of application No. PCT/FR97/01250, filed on Jul. 9, 1997.

(30) Foreign Application Priority Data

Jul. 16, 1996 (FR) ............................................. 96 08889

(51) Int. Cl.$^7$ .......................... C12Q 1/68; C12P 19/34; C12N 1/20; C12N 15/00; C07H 21/02
(52) U.S. Cl. ....................... 435/6; 435/91.1; 435/252.3; 435/254.11; 435/320.1; 536/23.1
(58) Field of Search .......................... 435/6, 91.1, 183, 435/252.3, 320.1, 455, 476; 436/94; 536/23.1, 24.3, 24.33, 25.3

(56) References Cited

U.S. PATENT DOCUMENTS

| | | | |
|---|---|---|---|
| 5,470,726 A | | 11/1995 | Miller et al. |
| 5,665,577 A | * | 9/1997 | Sodroski et al. ............. 435/456 |
| 5,681,746 A | * | 10/1997 | Bodner et al. .............. 435/350 |
| 6,312,948 B1 | * | 11/2001 | Cohen-Haguenauer ... 435/320.1 |

FOREIGN PATENT DOCUMENTS

| | | | |
|---|---|---|---|
| WO | WO 93/03143 | * | 2/1993 |
| WO | WO 93/10218 | | 5/1993 |
| WO | WO 94/13824 | | 6/1994 |
| WO | WO 96/17071 | | 6/1996 |

OTHER PUBLICATIONS

Izumi et al., Blasticidin S–resistance gene (bsr): a novel selectable marker for mammalian cells. Experimental Cell Research, 197, 299–233, 1991.*
Mulsant et al., Phleomycin resistance as a dominant selective marker in CHO cells. Somatic Cell and Molecular Genetics, 14, 243–252, 1988.*
Takahara et al.; "A New Retrovirus Packaging Cel . . . " Journal of Virology, vol. 66, No. 6, pp 3725–3732, Jun. 1992.
Manservigi, et al.; "Constitutive Expression in Human Cells . . . ", Virlogy, vol. 167, No. 1, pp. 284–288, Nov. 19888.
Noquiez–Hellin et al.; "Plasmoviruses: Nonvirul/viral vectors . . . " Proc. Natl. Acad. Sci. USA vol. 93, pp. 4175–4180.
Sitbon et al.; "Hemolytic anemia and erthroleukemia . . . " Cell vol. 47, pp. 851–859.

* cited by examiner

*Primary Examiner*—Kenneth R. Horlick
*Assistant Examiner*—Frank Lu
(74) *Attorney, Agent, or Firm*—Birch, Stewart, Kolasch & Birch, LLP

(57) ABSTRACT

The invention concerns a packaging eukaryotic cell for the production of defective infectious viruses carrying a transgene, characterized in that it is deficient in one cell function essential to its growth, in particular in the presence of a selection culture medium, the function being capable of being restored by the expression of an exogenous sequence introduced in the cell: either with a vector carrying transcomplementing functions of packaging cells; or with a vector carrying a transgene, and enabling the selection in a selective medium of cells carrying the said exogenous sequence.

11 Claims, 1 Drawing Sheet

HIGHLY PRODUCTIVE PACKAGING LINES

This application is a continuation of application Ser. No. 09/231,834, filed on Jan. 15, 1999, now abandoned, for which priority is claimed under 35 U.S.C. §120. application Ser. No. 09/231,834 is a continuation under 35 U.S.C. §4.120 of PCT International Application No. PCT/FR97/01250 filed on Jul. 9, 1997. The entire contents of each of the above-applications are hereby incorporated by reference. This application also claims priority of Application No. 96/08889 filed in France on Jul. 16, 1996 under 35 U.S.C. §119.

The invention relates to novel cell lines known as packaging lines which produce high titers of recombinant retroviruses which can be used in man for gene therapy.

Gene transfer by recombinant retroviruses is routinely used both in experimental work and in therapeutic trials.

Retroviral vectors used in such different situations are normally produced by packaging or transcomplementation lines, the terms having the same significance; such lines are cells which have been transduced with genetic constructions enabling constitutive expression of the different proteins required for the production of a retroviral particle containing structural proteins and the enzymes necessary for their infectivity. The aim of a packaging line is to provide helper functions by transcomplementation, in particular the genes coding for the proteins gag, pol and env, which have been removed from the genomic vector carrying a transgene the expression of which is desired by using a defective infectious virus. Such helper functions, which are free of the Ψ sequence, are stably expressed in packaging cells after transfection of one or more plasmids containing them and the RNA transcripts of which are not packaged into viral particles because the packaging sequence Ψ has been deleted. When such packaging cells are then transfected by vectors carrying a transgene, the gag viral proteins produced by the packaging cell can package the retroviral vector carrying the transgene into viral particles which are then released into the environment (see Miller A. D., Gene Therapy 1990 1: 5–14).

Different types of packaging lines have been produced using this general principle and are currently widely used. However, such lines are far from being optimised, in particular as regards their use for a specific transgene or for particular procedures. In particular, there is no means for causing transduced cells administered to patients to disappear if the transgene or its expression product induces undesirable effects (by inadequate expression or inappropriate insertion). Safety reasons constitute a further aspect for which it is important to have available packaging cells which can be destroyed if needed, since recombinations could lead to the formation of infectious viruses from packaging lines.

The choice of starting cells in which packaging lines can be produced is extremely important as regards the expected properties and their potential clinical use. The majority of cell lines in current clinical use are derived from fibroblasts of murine origin, NIH-3T3 cells. The interest in such cells is that they have been completely characterized, that they are not transformed (they do not produce tumour when re-injected in vivo), and they originate from animals which have been bred for many generations and which are known not to have particular diseases (for example neurodegenerative) which would cause the presence of a transmissible infectious agent to be suspected in such animals, and thus potentially in the cells used. Further, using murine cells offers a supplemental degree of safety in the event of contamination by an unknown transmissible infectious agent because of the species restriction which is often observed in infectious pathology. However, one problem with murine cells is that the viruses produced by such cells and the cells themselves are usually rapidly neutralised by human complement. A simple means for overcoming that problem is to produce packaging cells from human cells or from another species which is resistant to human complement.

However, human cells are often transformed and thus have tumoral potential. Further, the origin of the cells and their possible contamination by infectious agents of unknown origin which would be capable of infecting man are clearly not known in detail.

Simian cells could be used as human cells for their property of producing viral particles which would not be destroyed by complement, but they suffer from the same drawbacks as human cells as regards the possible presence of infectious agents.

Murine cells may exist into which genes have been transferred which endow the cells with greater resistance to complement and/or to human serum.

Such genes may be CD46, CD55, $C_1$ inhibitor ($C_1INH$), H protein, or soluble $CR_1$, in particular in a multimeric form as described in French patent FR-95 08901.

The present invention aims to provide means for preparing novel packaging lines which at least partially overcome one or more of the problems described above and which are capable of:

producing high titers of recombinant retroviruses;

being well tolerated;

being resistant to the complement while remaining acceptable as regards safety;

being produced easily using good manufacturing practices and having an expression stability of at least three months;

incorporating a selection gene which allows a positive selection of cells from blood cells which have incorporated the vector carrying the transgene;

having a safety system enabling cells to be destroyed as needed.

In order to satisfy these different requirements, the choice of starting cell lines must first be optimised, also the choice of each of the constituents required to obtain the defective infectious recombinant retroviral particle, in particular the choice of vectors enabling the packaging cell to produce the gag, pol and env proteins of the retrovirus.

Regarding mass production of these cells under good manufacturing practice (GMP) conditions for cell or virus production for clinical use, cells for which the growth characteristics are completely known are required, which have short division times, and with high growth density, in suspension if necessary.

Finally, it is necessary to select stable transfectants from the cells used, which transfectants express the different transgenes of interest. Currently, packaging cells are transduced by means of a single vector carrying the gene of interest and a selection gene, or two separate vectors. During subsequent culture of the transduced cells, it is generally necessary to maintain selection pressure so as not to lose the transgene of interest. However, it is known that different types of modification can lead to a loss of expression of the therapeutic gene, even in the presence of this selection. This is particularly true when the transgene has a certain toxicity thus endowing the rare cells which have lost it with a selective advantage. The possible use of cells which are deficient in certain enzymes enabling their selection on this criterion would thus be an additional advantage, especially when the therapeutic gene of interest complements the deficiency. In other words, the use of a gene supplementing a genetic deficiency in the cell as a selection gene instead of a gene resistant to a toxin (in general an antibiotic) has a number of advantages, one of which is the possibility of cultivating said cells in the absence of the toxin. Further, if the gene is also the gene of interest, it is no longer possible to lose it during selection even it has a selective disadvantage. This gene can also be a "safety" gene or "suicide" gene which means that the expression product of that gene in the presence of an exogenic substance leads to specific destruction of the cell.

The invention thus provides eukaryotic packaging cells for the production of defective infectious viruses carrying a transgene, characterized in that they are deficient in a cellular function which is essential for their growth, in particular in the presence of a selective culture medium, said function being capable of being restored by expression of an exogenous sequence introduced into the cell:

either with a vector carrying functions which are transcomplementary to the packaging cells;

or with a vector carrying the transgene;

expression of the exogenous sequence thus introduced into the cell permitting selection of cells carrying said sequence in a selective medium.

The eukaryotic packaging cell of the invention is characterized in that it has one or more of the following properties:

it can produce viral particles in an amount of more than $10^5$ particles per ml;

it is resistant to the complement or it produces viral particles which are resistant to the complement;

it has a division period of less than 30 hours;

it is stable for at least three months in a non selective culture medium;

it is free of endogenous retroviruses.

The invention also relates to packaging lines producing defective infectious viruses, carrying a gene of therapeutic interest in which the gene of interest itself, carried by a suitable vector, is used as a selection gene for the packaging line which can produce the defective recombinant viruses.

A number of cell types can be used on this basis: NIH-3T3TK⁻ cells:

a) NIH-3T3 murine cells which are currently widely used as packaging cells producing recombinant retroviruses in clinical use (Takahara et al., Journal of Virology, (June 1992), 66 (6) 3725–32).

b) TK⁻ cell lines have already been described, including NIH-3T3 TK[31] cells (F. Wagner et al., EMBO Journal (1985), Vol. 4 n°3, pages 663–666); these cells can be killed when they are cultivated in selective culture media such as HAT. If they are complemented for the kinase thymidine function, for example those from the HSV1-TK virus, they can grow in a selective medium; such lines thus offer the possibility of using the HSV1-TK gene as a selection gene. The gene coding for the thymidine kinase of HSV1 or one of its functional derivatives is also widely used as a transgene as a pro-drug transforming ganciclovir or acyclovir into a drug which is cytotoxic for the cell, and it can thus be applied to selective cell destruction, for example of cancerous cells (see, for example, International patent application WO 95/22617).

More generally, TK⁻ cells can be derived by mutating any cell which can be used as a packaging cell, for example Vero cells.

Thus when the therapeutic cell carried by the expression vector is introduced into a packaging cell which is deficient as regards thymidine kinase, the packaging cell which has integrated the vector carrying the transgene is selected on the therapeutic gene itself, thus enabling the productivity of the defective recombinant virus culture to be increased; packaging cells which have not integrated the recombinant vector are ipso facto eliminated in a selective medium.

More generally, the invention relates to packaging cells which are deficient in a cellular function which is essential for their growth and in which the transgene can restore the deficient cellular function.

It is important that the defective recombinant infectious vectors carrying a transgene are resistant to the complement and to other factors which are potentially destructive to the virus or to the cells in the blood or in interstitial fluids; to this end, the cell lines of the invention are themselves advantageously resistant to the complement and thus preferably originate from human cells or simian cells and more particular from Old World apes or modified human cells.

In the case of human or simian cells, it is important to have available cells with a clear origin, namely which do not carry infectious agents of unknown origin which can infect man. The 143 B TK⁻ line is a known human origin line (Manservigi R. et al., Virology (November 1988), 167 (1) 284–8); it has a short division period, i.e., of about eighteen hours, and it produces viral particles which are complement resistant. It can thus advantageously be used as a packaging cell of the invention. Vero cells are also widely used, in particular for vaccine production; they are simian cells which also produce viral particles which are resistant to neutralisation by the complement; the culture conditions for these lines are completely known and a thymidine kinase deficient cell line can be obtained using conventional techniques and can advantageously be used after transformation with vectors enabling packaging construction, as a packaging cell line having the characteristics of the cell lines of the invention.

The function of a cell line packaging a retrovirus is to provide transcomplementary functions which have been deleted from the recombinant vector carrying the transgene, these functions essentially being the genes coding for the gag, pol and env proteins. These functions are stably expressed in packaging cells from one or preferably two distinct plasmids in order to very substantially reduce the possibility of generating recombinant particles which are able to replicate. Existing packaging lines have been produced from murine or avian retroviral proteins and have been described by Miller A. D., Hum. Gene Ther, 1990 1: 5–14.

The gag and pol murine retrovirus genes are normally synthesised by the same RNA which gives rise to gag precursors or gag/pol precursors by shifting the reading frame. These processes are optimised in the Moloney type retroviral particle and constructions intended to make the packaging cell of the invention do not affect the gag/pol LTR structure with the exception of the Ψ deletion. The choice of gag/pol genes and of the LTRs depends on the aim to be achieved, which is to produce a large amount of defective recombinant viral particles, and as a result the largest possible expression of gag/pol genes is sought.

In one embodiment of the invention, the packaging cells are characterized in that they comprise:

a vector carrying an LTR itself characterized by good transcription activity, for example the LTR from the FB29 Friend virus (see International patent application WO 96/17071):

a gag/pol region originating either from the Moloney virus or from the Friend virus or from any other retrovirus where the structure and expression of this function are optimised;

c) a quantitative selection gene, i.e., such that when the selection pressure is increased, the number of transcripts which are synthesised is increased a priori.

If the quantitative type selection gene is located on the same plasmid as the plasmid coding for gag and pol, the increase in the number of transcripts coding for the selection gene increases in the same way as the number of transcripts coding for gag and pol. Optimisation will be still further improved if it is ensured that translation of the selection gene is weaker than that of gag/pol.

To this end, the selection gene is located either at about a hundred base pairs from the pol stop codon, or under the control of a normal or mutated IRES sequence (Internal Ribosome Entry Sites) such that translation initiation is less efficient than that of the gag and pol genes. Mutation can consist of removing the main ATG, and initiation thus occurs on a less efficient ATG which is pre-existing or generated by mutation.

IRES sequences are sequences which are used in retroviral constructions to control translation of polycystronic RNA transcripts. The IRES sequences can directly initiate translation in a start codon. Thus inclusion of such a sequence can enable a number of genes to be expressed from the same promoter.

The other alternative, which is to locate the selection gene at about a hundred base pairs from the pol stop codon, can also attenuate translation of the selection gene with respect to translation of gag/pol genes.

The selection gene can also be located on the vector carrying the env gene when the latter is distinct from that carrying gag/pol; finally, the two construction vectors of the packaging cell can each carry a selection gene.

The selection genes can, for example, be BSR type genes, i.e., a blasticidine S resistance gene, or a zeomycin resistance gene. The gene for blasticidine resistance is a selection gene for animal cells which have in particular been described by IZUMI M. et al. in Experimental Cell Research (1991), 197: 229–233. This gene appears to be particularly effective since it has been used as a selection marker to produce hybridomes producing good yields of human monoclonal antibodies (Journal of Immunological Methods, 1994, 177:17–22).

These and other aspects and embodiments of the invention will become evident upon reference to the following detailed description and attached figures.

Figure 1A:
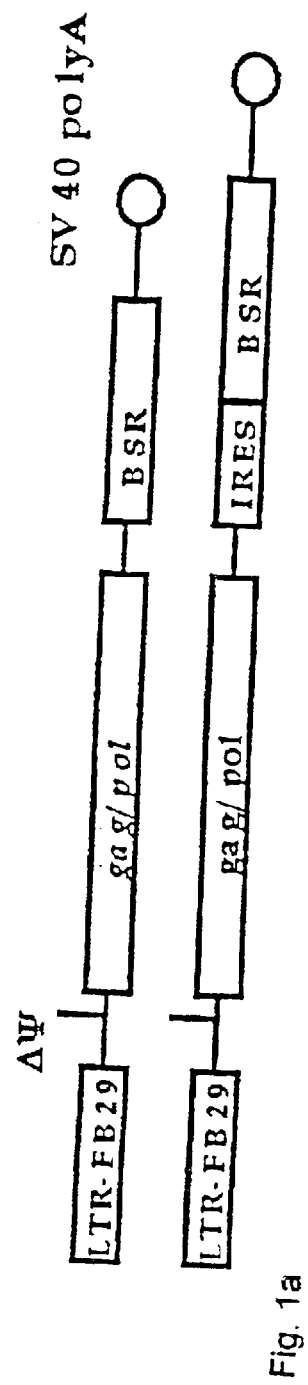
FIG. 1A is a diagram of a suitable vector for constructing packaging lines according to the invention.

One example of a particularly suitable vector for constructing the packaging lines of the invention is shown in FIG. 1a.

The second vector which can be used to construct the packaging cell carries genes coding for retrovirus envelopes. The majority of genes coding for retrovirus envelopes could have a certain amount of toxicity for the cell; sufficient quantities of envelope proteins are required which are synthesised so that the defective recombinant retroviral particles are properly infectious.

Env sequences coding for envelope peptide derivatives, for example enphotrope, can, for example, be the 407a envelope of the Moloney murine leukaemia virus (MoMuLV). However, any type of gene coding for an envelope protein which can be integrated into the cell membrane when the retrovirus buds can be used; the choice of the env protein can be guided by the nature of the receptor in the target cell which is to be transfected by the defective recombinant retroviral virus. The env gene carried by the construction plasmid of the packaging cell is under the control of viral or non viral transcription regulating sequences. As regards genetic constructions, it may be a strong promoter such as the cytomegalovirus (CMV) promoter so that pre-selection forces the cell to synthesise large amounts of envelopes. The term "strong promoter" means any nucleic acid sequence comprising the RNA polymerase binding site and binding sites for regulating proteins and permitting a large degree of transcription of the sequence located under the control of said promoter.

It may also be an inducible promoter which would allow the absence of or only a small amount of envelope expression which could then be temporarily induced when collecting the viral particles. The term "inducible promoter" means a promoting sequence which can be activated as desired by a given molecule; this type of promoter is used whenever it is desired to express a given gene on demand.

Examples of inducible promoters which can be used in constructing the packaging cells of the invention are tetracycline-inducible promoters described by Bujard et al. in Mol. and Gen. Genetics, (Dec. 9, 1977) 157 (3): 301–11, or conditional inducible promoters such as the RAR-β promoter (Japanese Journal of Genetics (June 1993) 68 (3) 175–84); "conditional promoters" are constituted by a promoting sequence activated by one or more trans-regulators specifically produced by a given tissue, but not necessarily identified, such as the insulin promoter which is sensitive to strictly pancreatic factors.

These constructions can be applied to all conventional type 4070A env genes of the Moloney murine leukaemia virus (MoMuLV) or to envelopes which could be used depending on their particular properties, in particular resistance to type RD114 complement. HTLV1 type envelopes or lentivirus derivatives such as foamy virus can also be used.

Envelope genes with a particular tropism for target cells which can be transfected by the defective recombinant viruses produced by the packaging cells can advantageously be used, for example spumavirus envelope sequences with a particular tropism for human haematopoietic cells.

Finally, in an inducible system as described above, type VSV-G envelopes can be used.

Figure 1B:
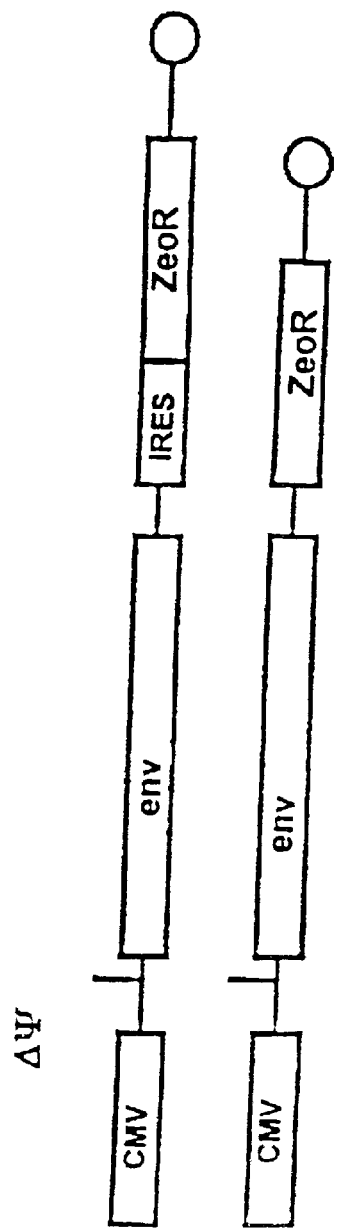
FIG. 1B is a diagram of a vector containing an env gene and ZeoR as the selection gene.

The vector carrying the env gene comprises a polyadenylation sequence such as that from SV40 virus at the 3' end. An example of a vector carrying the env gene is shown in FIG. 1b, in which ZeoR is the zeomycin resistance gene.

The two vectors which can constitute the packaging cells are, of course, free of packaging sequences.

The different embodiments of the recombinant packaging cells as described above can be transfected by a recombinant retroviral vector for expression in and/or integration into the genome of a target cell of a nucleotide sequence (transgene) selected for therapeutic interest. This transgene can be either a sequence coding for a function which is deficient in the target cell, which function it is desired to restore, or to introduce a complementary and/or regulating function into the target cell, or (and this is not limiting), a sequence which can activate prodrugs as is the case for the thymidine kinase gene of the HSV1 virus transforming ganciclovir or acyclovir into a toxic drug which destroys cells, or the cytosine deaminase gene transforming a 5-fluorouracil precursor into an active drug; finally, it can be a transgene which can induce or stimulate the immune system, either by manipulation of tumour cells, or by manipulation of the cells of the immune system itself or, in contrast, a transgene which can specifically inhibit an immune response in the case, for example, of graft rejection or for auto-immune diseases.

The general structure of a retroviral gene carrying a transgene requires the presence of two LTRs surrounding the gene or genes of interest or transgenes and carrying the region enabling packaging of the transcript in the pseudo-retroviral particle the structure proteins of which are coded by the packaging cell of the invention.

Preferred LTRs are those deriving from Moloney strains such as those from Mov strains (see Jaenish) because of their greater capacity to express in slightly or non differentiated cells (tumour cells, inter alia), also those described in European patent application EP-A-0 674 716 where the LTRs are derived from Friend virus because of their greater degree of expression, as was described above.

The invention also relates to recombinant retroviral vectors carrying a heterologous gene the expression of which in a host cell is sought, characterized in that they comprise:

a gene of therapeutic interest X, under the control of a promoter;

a nucleotide sequence Y the expression of which complements the deficient function in the packaging cell;

a packaging sequence Ψ;

if necessary, a safety gene Z the expression of which in the presence of an exogenous substance leads to the destruction of the transfected or infected cell.

When the transgene of therapeutic interest is a suicide gene, for example that coding for HSV1-TK or one of its functional derivatives, the X and Y or Y and Z sequences form one and the same gene, and the use of such a vector enables said packaging cells which have been transfected by said vector to be selected.

A good viral titer depends on the number of packagable transcripts produced by the packaging cell.

The invention further relates to a method of producing high titers of defective infectious recombinant vectors in cells as described above, the method comprising:

a) infecting or transfecting said cells by a recombinant vector carrying at least one gene X of therapeutic interest;

a nucleotide sequence Y the expression of which complements the deficient function in the packaging cell if this deficiency subsists after construction of said packaging cell by vectors carrying the gag, pol and env genes;

a packaging sequence Ψ;

if necessary, a safety gene Z the expression of which in the presence of an exogenous substance leads to the destruction of the transfected or infected cell;

b) selecting said cells in a selective culture medium when the packaging cell is deficient in a given function and the vector carrying the transgene supplements this deficiency.

When the packaging lines are deficient in thymidine kinase, the vector carrying the transgene will be a bicistronic vector enabling selection in the presence of a thymidine kinase gene of HSV1 or a functional derivative thereof. A surprising property of the HSV1-TK gene is that a high degree of expression can be toxic for the cell, preventing a large number of transcripts from being produced. In this case of gene toxicity, selection of producing cells results in the production of clones in which gene expression is low and thus the infectious titer is very low. The vector of the invention, which can infect or transfect the packaging cells described above, will thus be constructed so that production of the packagable transcripts of the transgene is high compared with the production of HSV1-TK genes. Thus a TK⁻ packaging cell transfected by a bicistronic vector carrying a transgene and HSV1-TK or one of its derivatives can both be selected in the selective medium HAT and produce high titers of viral particles, while avoiding counter-selection due to the toxic activity of HSV1-TK when the gene is actively translated. This thus enables packaging cells with a high titer to be produced and which produces defective retroviruses coding either for HSV1-TK alone or for a gene of interest and HSV1-TK.

This difference in the production of transcripts of transgene X and of transgene Y is produced by constructing recombinant vectors in which the nucleotide sequence Y the expression of which complements the deficient function of the packaging cells, for example HSV1-TK, is located either at about a hundred base pairs from the stop codon for the transgene, or under the control of a normal or mutated IRES type sequence as described above such that initiation of translation of the Y sequence is less efficient than that of the X sequence.

When the transgene is itself the gene enabling selection of the packaging cells, i.e., in the case when X and Y are one and the same gene (for example HSV1-TK), the gene of interest itself is used as the selection gene. In contrast, when gene X and gene Y are different, gene Y can then also carry out the function of a safety gene Z as if necessary it can destroy cells transfected with the therapeutic gene by treating the patient with a substance which transforms the prodrug into a toxic drug.

Figure 2:
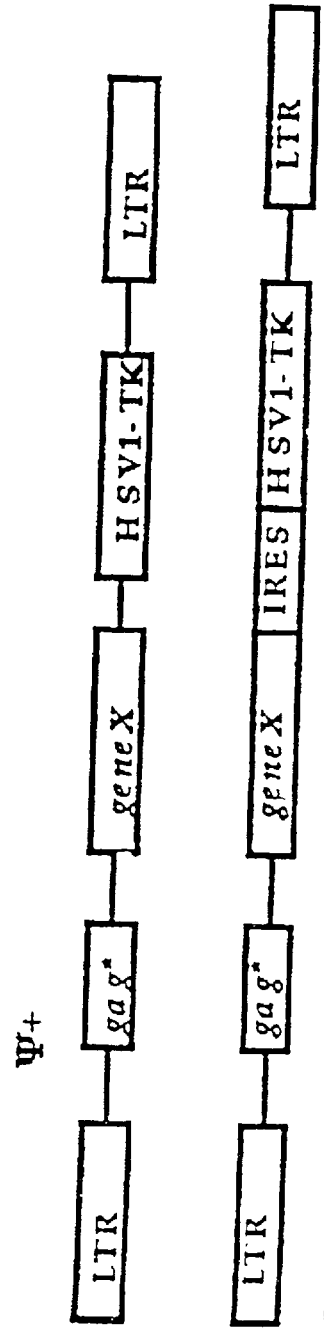
FIG. 2 is a graphic representation of an embodiment of a recombinant vector according to the invention.

When the Y sequence and as the case may be the Z sequence code for HSV1-TK, an embodiment of the recombinant vector of the invention is shown in FIG. 2.

In this figure, the two vectors represented show the difference between the two embodiments enabling low expression of the HSV1-TK gene (sequences Y and Z combined), either by a certain distance from the stop codon for gene X, or by introducing an IRES sequence. The sequence represented by gag* means that the packaging sequence can comprise not only the genetic region required for packaging but also the portion of the mutated gag gene which does not enable the gag protein to be reconstituted but which increases packaging efficiency.

The properties of HSV1-TK are compatible with this concept. Very small quantities of TK are sufficient to be able to select cellular clones derived from negative TK cells in the presence of selective HAT medium; in the same way, a very low TK expression is sufficient to obtain good sensitivity to ganciclovir.

In some cases, the three genes X, Y and Z can represent just one gene such as the HSV1-TK gene which acts both as a transgene, a selection gene, and a safety gene. This type of construction has the advantage of enabling a second therapeutic gene to be added to the vector, for example a gene which codes for cytokines when cancerous cells are to be eliminated.

A further embodiment of the invention, when the TK gene is the therapeutic gene itself, is characterized in that the Y gene is a gene coding for a further selection marker, for example the BSR gene cited above, or a further gene of therapeutic interest such as a cytokine gene.

For optimal expression of the Y gene, this latter can be placed under the control of a weak internal promoter which can itself be attenuated by a read-through by the LTR of the retroviral vector. In this state, the 3' end of the vector LTR can also contain an amplifier deletion such that the read-through does not prevent expression after infection of the target cell by recombinant viral particles.

In general, the method for producing high titers of defective recombinant virus can be applied to any transgene the absence of which induces a negative selection pressure for the packaging cell; a cell thus deleted from the gene coding for this transgene will then be "saved" by the retroviral vector which would at the same time act as a selection vector. This would be applicable to any cellular gene the overexpression of which induced a negative selection pressure for the cell since only packaging cells carrying and producing recombinant retroviruses would be positively selected even when expression of the gene of interest would tend to counter-select these cells.

The invention concerns the use of packaging cells and vectors as described above for preparing a gene therapy drug with safety properties, and the efficiency required for that type of drug, namely resistance to complement, and with the possibility of being destroyed in situ as needed.

The invention also concerns the use of the packaging cells of the invention and recombinant vectors carrying a gene of interest as described above for transforming target cells of the immune system such as haematopoietic strains, lymphocyte cells or cancerous cells.

The invention further concerns the use of packaging cells as described above in a method for co-culturing target cells of a defective infectious retrovirus carrying a gene of interest to gene therapy and produced by the packaging cells, the latter having to be destroyed before use of said thus transformed target cells in drugs. It is known that certain indications require this in vitro co-culture of the target cell and the packaging cell, for example when the target cell is a lymphocyte system cell or haematopoietic strain cells. The packaging cell must be eliminated before re-introducing the transformed target cell. When the packaging cell carries the HSV1-TK gene as a selection gene, for example, the use of a culture medium containing HAT in the presence of ganciclovir and acyclovir can selectively destroy cells carrying the HSV1-TK gene and thus the packaging cell to the advantage of only the target cells transfected by the retroviral virus produced by said packaging cells.

A further implementation regarding co-culture involves packaging cells directly deprived of the HSV1-TK gene and selection of the cellular mixture in the presence of HAT selective medium by maintaining a suitable cell concentration which can again cause the packaging cells to disappear without altering the target cells.

What is claimed is:

1. A packaging cell line for the production of defective infectious retroviruses, wherein said packaging cell line is a human cell comprising, in its genome, at least two retroviral vectors:
   (a) wherein the first retroviral vector comprises, under the control of a LTR (Long Terminal Repeat) type promoter, the sequence of retroviral gag/pol genes, a mutated or normal IRES (Internal Ribosome Entry Sites) sequence, the sequence of a first selection gene, and a polyadenylation sequence;
   (b) wherein the second retroviral vector comprises, under the control of a promoter, the sequence of a gene coding for an envelope protein, a mutated or normal IRES sequence, the sequence of a second selection gene and a polyadenylation sequence; and
   (c) said first and second vectors being free of a retroviral packaging sequence.

2. The packaging cell-line according to claim 1, wherein the first selection gene is selected from a blasticidine S resistance gene (BSR gene) and a zeomycine resistance gene (ZeoR gene).

3. A method for producing high titres of recombinant viruses in the packaging cell-lines as defined in claim 1, comprising:
   (a) infecting or transfecting said cell line by a recombinant vector comprising:
      (a1) a gene of therapeutic interest X, under the control of a promoter;
      (a2) a nucleotide sequence Y, the expression of which complements a deficient function in the packaging cell; and
      (a3) a packaging sequence Ψ,
   (b) selecting said cell line in a culture medium causing cell death when the sequence Y is not expressed.

4. A packaging cell line for the production of defective infectious retroviruses, wherein said packaging cell line is a human cell comprising, in its genome, at least a first and a second viral constructs,
   said first viral construct comprising, operably linked, a promoter, the sequence of retroviral gag/pol genes, a mutated or normal IRES (Internal Ribosome Entry Sites) sequence, the sequence of a first selection gene and a polyadenylation sequence,
   said second viral construct comprising, operably linked, a promoter, the sequence of a gene coding for an envelope protein, a mutated or normal IRES sequence, the sequence of a second selection gene and a polyadenylation sequence,
   said first and second constructs being free of a retroviral packaging sequence.

5. The cell line of claim 4, wherein the envelope protein encoded by said second viral construct is a 4070A envelope protein.

6. The cell of claim 4, wherein the IRES sequence in said first and second viral constructs is a mutated IRES sequence.

7. A packaging cell line for the production of defective infectious viruses, wherein said packaging cell line is a human cell comprising, in its genome, at least a first a second viral constructs,
   said first viral construct comprising, operably linked, a retroviral LTR (Long Terminal Repeat) type promoter sequence, the sequence of retroviral gag/pol genes, a mutated or normal IRES (Internal Ribosome Entry Sites) sequence, the sequence of a first selection gene selected from the group consisting of a blasticidine S resistance gene (BSR gene) and a zeomycine resistance gene (ZeoR gene), and a polyadenylation sequence,
   said second viral construct comprising, operably linked, a cytomegalovirus (CMV) promoter, the sequence of a gene coding for an envelope protein, a mutated or normal IRES sequence, the sequence of a phleomycine resistance gene and a polyadenylation sequence, said first and second constructs being free of a retroviral packaging sequence.

8. The cell line of claim 7, wherein the envelope protein encoded by said second viral construct is a 4070A envelope protein.

9. The cell line of claim 7, wherein the IRES sequence in said first and second viral constructs is a mutated IRES sequence.

10. The cell line of claim 7, wherein the LTR type promoter sequence in said first viral constructs is the LTR of a FB29 Friend virus.

11. A method of producing recombinant retroviruses, comprising infecting or transfecting a packaging cell line of claim 4 with a recombinant retroviral vector and collecting the recombinant retroviruses produced.

* * * * *